(12) United States Patent
Hagn

(10) Patent No.: US 12,376,934 B2
(45) Date of Patent: Aug. 5, 2025

(54) SURGICAL ROBOTIC ARM STORAGE ASSEMBLIES AND METHODS OF REPLACING SURGICAL ROBOTIC ARMS USING THE STORAGE ASSEMBLIES

(71) Applicant: Covidien LP, Mansfield, MA (US)

(72) Inventor: Ulrich Hagn, Munich (DE)

(73) Assignee: Covidien LP, Mansfield, MA (US)

( * ) Notice: Subject to any disclaimer, the term of this patent is extended or adjusted under 35 U.S.C. 154(b) by 825 days.

(21) Appl. No.: 17/609,152

(22) PCT Filed: May 19, 2020

(86) PCT No.: PCT/US2020/033532
§ 371 (c)(1),
(2) Date: Nov. 5, 2021

(87) PCT Pub. No.: WO2020/236778
PCT Pub. Date: Nov. 26, 2020

(65) Prior Publication Data
US 2022/0296328 A1    Sep. 22, 2022

Related U.S. Application Data

(60) Provisional application No. 62/851,341, filed on May 22, 2019.

(51) Int. Cl.
| | |
|---|---|
| *A61B 50/30* | (2016.01) |
| *A61B 34/30* | (2016.01) |
| *A61B 50/13* | (2016.01) |
| *A61B 50/26* | (2016.01) |
| *A61B 90/50* | (2016.01) |

(52) U.S. Cl.
CPC .............. *A61B 50/30* (2016.02); *A61B 34/30* (2016.02); *A61B 50/13* (2016.02); *A61B 50/26* (2016.02); *A61B 90/50* (2016.02)

(58) Field of Classification Search
CPC ......... A61B 50/30; A61B 34/30; A61B 50/13; A61B 50/26; A61B 90/50
See application file for complete search history.

(56) References Cited

U.S. PATENT DOCUMENTS 3,871,521 A    3/1975   Szatkowski
5,447,230 A *  9/1995   Gerondale ............. A61B 50/30
                                                         206/467

(Continued)

FOREIGN PATENT DOCUMENTS

| EP | 2695822 A1 | 2/2014 |
|---|---|---|
| WO | 2018108860 A1 | 6/2018 |
| WO | 2019067028 A1 | 4/2019 |

OTHER PUBLICATIONS

Supplementary Partial European Search Report dated Jun. 12, 2023 for European Patent Application No. 20808794.0 (14 pages).

(Continued)

*Primary Examiner* — Zakaria Elahmadi
(74) *Attorney, Agent, or Firm* — Carter, DeLuca & Farrell LLP

(57) ABSTRACT

A storage assembly for a surgical robotic arm includes a stand, legs configured to be coupled to a bottom end portion of the stand, and a handle slidably coupled to the stand. The stand is configured to receive and support a surgical robotic arm therein when in vertical and horizontal positions.

8 Claims, 10 Drawing Sheets

(56) References Cited

U.S. PATENT DOCUMENTS

| | | | |
|---|---|---|---|
| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,357,774 | B2 | 4/2008 | Cooper |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,391,173 | B2 | 6/2008 | Schena |
| 7,398,707 | B2 | 7/2008 | Morley et al. |
| 7,413,565 | B2 | 8/2008 | Wang et al. |
| 7,453,227 | B2 | 11/2008 | Prisco et al. |
| 7,524,320 | B2 | 4/2009 | Tierney et al. |
| 7,574,250 | B2 | 8/2009 | Niemeyer |
| 7,594,912 | B2 | 9/2009 | Cooper et al. |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |
| 8,418,073 | B2 | 4/2013 | Mohr et al. |
| 8,419,717 | B2 | 4/2013 | Diolaiti et al. |
| 8,423,182 | B2 | 4/2013 | Robinson et al. |
| 8,452,447 | B2 | 5/2013 | Nixon |
| 8,454,585 | B2 | 6/2013 | Whitman |
| 8,499,992 | B2 | 8/2013 | Whitman et al. |
| 8,508,173 | B2 | 8/2013 | Goldberg et al. |
| 8,528,440 | B2 | 9/2013 | Morley et al. |
| 8,529,582 | B2 | 9/2013 | Devengenzo et al. |
| 8,540,748 | B2 | 9/2013 | Murphy et al. |
| 8,551,116 | B2 | 10/2013 | Julian et al. |
| 8,562,594 | B2 | 10/2013 | Cooper et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |
| 8,600,551 | B2 | 12/2013 | Itkowitz et al. |
| 8,608,773 | B2 | 12/2013 | Tierney et al. |
| 8,620,473 | B2 | 12/2013 | Diolaiti et al. |
| 8,624,537 | B2 | 1/2014 | Nowlin et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,666,544 | B2 | 3/2014 | Moll et al. |
| 8,668,638 | B2 | 3/2014 | Donhowe et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,758,352 | B2 | 6/2014 | Cooper et al. |
| 8,761,930 | B2 | 6/2014 | Nixon |
| 8,768,516 | B2 | 7/2014 | Diolaiti et al. |
| 8,786,241 | B2 | 7/2014 | Nowlin et al. |
| 8,790,243 | B2 | 7/2014 | Cooper et al. |
| 8,808,164 | B2 | 8/2014 | Hoffman et al. |
| 8,816,628 | B2 | 8/2014 | Nowlin et al. |
| 8,821,480 | B2 | 9/2014 | Burbank |

(56) References Cited

U.S. PATENT DOCUMENTS

| | | |
|---|---|---|
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,138,297 B2 * | 9/2015 | Brisson .................. A61B 34/30 |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,724,165 B2 * | 8/2017 | Arata .................... A61B 34/71 |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,165 B2 | 10/2018 | Power |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |

(56) References Cited

U.S. PATENT DOCUMENTS

| | | | |
|---|---|---|---|
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,376,002 B2 | 7/2022 | Shelton, IV et al. |
| 11,376,098 B2 | 7/2022 | Shelton, IV et al. |
| 11,381,759 B2 | 7/2022 | Zhao et al. |
| 11,382,621 B2 | 7/2022 | Scheib et al. |
| 11,382,624 B2 | 7/2022 | Harris et al. |
| 11,382,625 B2 | 7/2022 | Huitema et al. |
| 11,382,626 B2 | 7/2022 | Shelton, IV et al. |
| 11,382,627 B2 | 7/2022 | Huitema et al. |
| 11,382,638 B2 | 7/2022 | Harris et al. |
| 11,382,644 B2 | 7/2022 | Schoettgen et al. |
| 11,389,160 B2 | 7/2022 | Shelton, IV et al. |
| 11,389,255 B2 | 7/2022 | DiMaio et al. |
| 11,399,906 B2 | 8/2022 | Shelton, IV et al. |
| 11,406,379 B2 | 8/2022 | Hess et al. |
| 11,410,259 B2 | 8/2022 | Harris et al. |
| 11,419,630 B2 | 8/2022 | Yates et al. |
| 11,424,027 B2 | 8/2022 | Shelton, IV |
| 11,432,888 B2 | 9/2022 | Diolaiti et al. |
| 11,432,893 B2 | 9/2022 | Itkowitz et al. |
| 11,432,895 B2 | 9/2022 | Loh et al. |
| 11,439,390 B2 | 9/2022 | Patel et al. |
| 11,439,391 B2 | 9/2022 | Bruns et al. |
| 11,468,791 B2 | 10/2022 | Jarc et al. |
| 11,471,155 B2 | 10/2022 | Shelton, IV et al. |
| 11,471,221 B2 | 10/2022 | Zhao et al. |
| 11,478,308 B2 | 10/2022 | Hoffman et al. |
| 11,490,977 B2 | 11/2022 | Schena et al. |
| 11,497,499 B2 | 11/2022 | Shelton, IV et al. |
| 11,504,119 B2 | 11/2022 | Shelton, IV et al. |
| 11,504,124 B2 | 11/2022 | Patel et al. |
| 11,510,743 B2 | 11/2022 | Shelton, IV et al. |
| 11,517,312 B2 | 12/2022 | Wixey |
| 11,517,325 B2 | 12/2022 | Shelton, IV et al. |
| 11,518,048 B2 | 12/2022 | Saraliev et al. |
| 11,564,760 B2 * | 1/2023 | Steger .................. A61B 90/50 |
| 11,589,939 B2 * | 2/2023 | Stricko, III ........... A61B 34/35 |
| 11,737,842 B2 * | 8/2023 | Griffiths ............... A61B 34/35 |
| | | 700/248 |
| 11,998,287 B1 * | 6/2024 | James ................... H04L 67/12 |
| 2009/0024142 A1 * | 1/2009 | Ruiz Morales ........ A61B 34/37 |
| | | 606/130 |
| 2009/0245600 A1 * | 10/2009 | Hoffman ............... A61B 34/37 |
| | | 348/240.99 |
| 2013/0204271 A1 * | 8/2013 | Brisson ................. A61B 34/30 |
| | | 606/130 |
| 2015/0136896 A1 * | 5/2015 | Beebe .................... H05K 5/03 |
| | | 428/80 |
| 2018/0333215 A1 * | 11/2018 | Timm ................... B25J 9/0009 |
| 2018/0361568 A1 * | 12/2018 | Cagle ..................... B62B 3/04 |
| 2018/0362060 A1 * | 12/2018 | Schaller ................ A61B 34/30 |
| 2022/0031407 A1 * | 2/2022 | Kapadia ................ A61B 34/74 |
| 2022/0273387 A1 * | 9/2022 | Reardon ................ A61B 34/37 |
| 2023/0255705 A1 * | 8/2023 | Murphy ................ A61B 34/20 |
| | | 606/1 |
| 2023/0310099 A1 * | 10/2023 | Ye ......................... A61B 90/57 |
| | | 606/1 |
| 2023/0310109 A1 * | 10/2023 | Timm ................... A61B 90/57 |
| | | 248/645 |

OTHER PUBLICATIONS

Chinese Office Action dated Dec. 4, 2023 for Chinese Patent Application No. 2020800369880 (16 pages).

Extended European Search Report dated Sep. 12, 2023 for European Patent Application No. 20808794.0 (14 pages).

International Search Report dated Sep. 7, 2020, issued in corresponding international application No. PCT/US2020/033532, 2 pages.

* cited by examiner

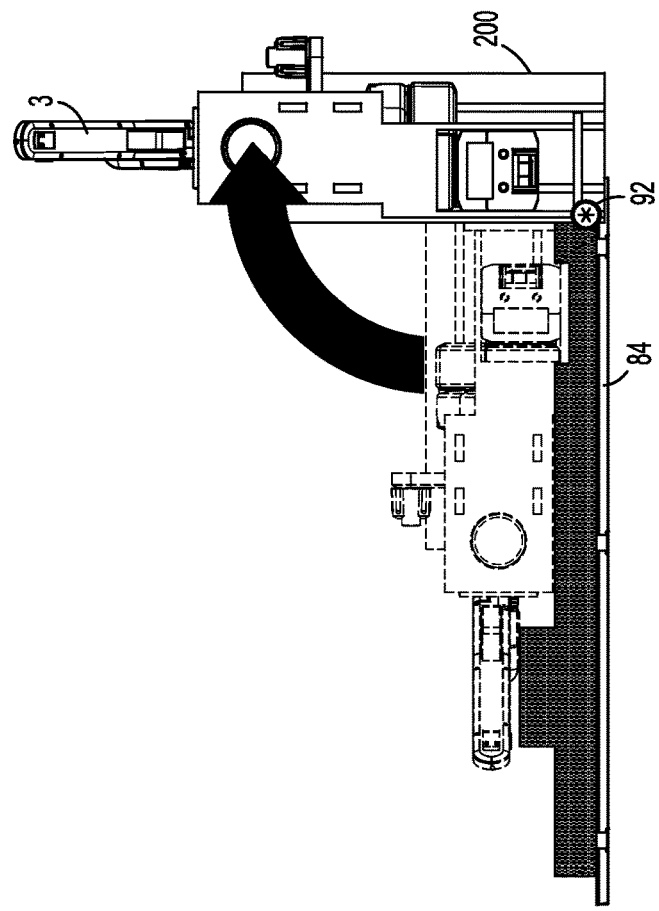
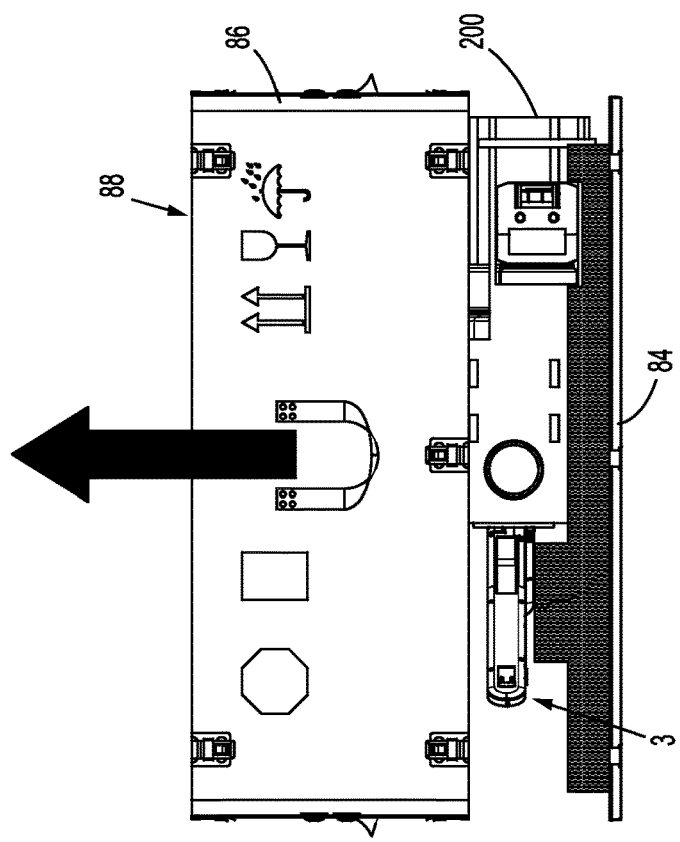
FIG. 6A
FIG. 6B

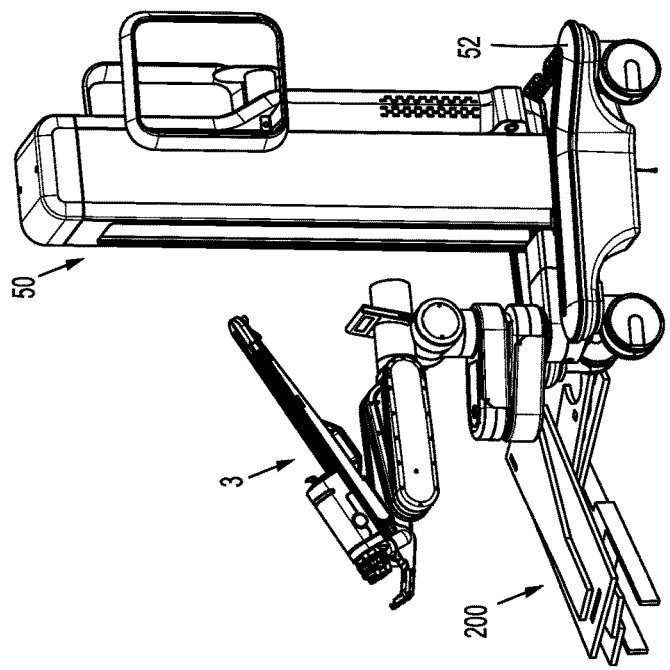
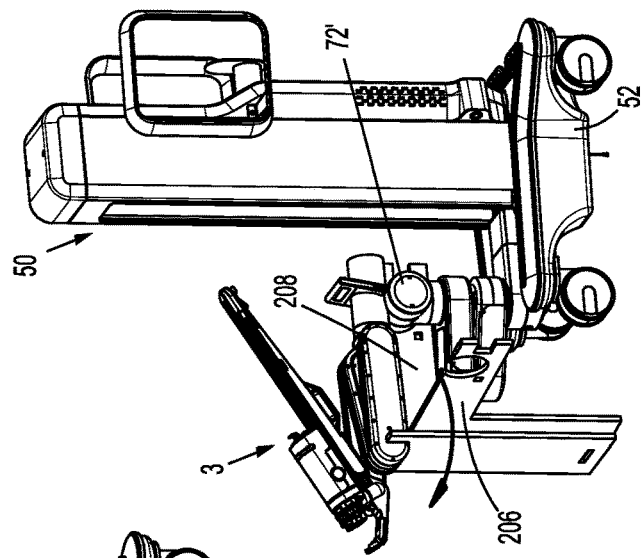
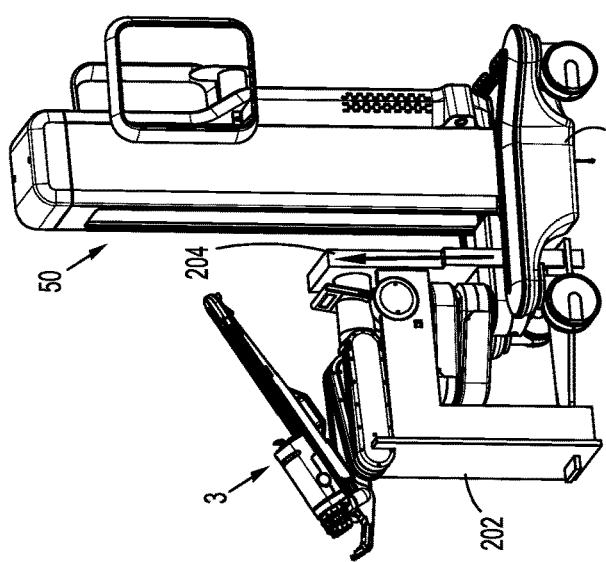
FIG. 8C
FIG. 8B
FIG. 8A

SURGICAL ROBOTIC ARM STORAGE ASSEMBLIES AND METHODS OF REPLACING SURGICAL ROBOTIC ARMS USING THE STORAGE ASSEMBLIES

CROSS-REFERENCE TO RELATED APPLICATION

This application is a National Stage Entry of PCT/US2020/033532, filed on May 19, 2020, which claims the benefit of and priority to U.S. Provisional Application No. 62/851,341, filed on May 22, 2019, the entire contents each of which are incorporated by reference herein.

BACKGROUND

Robotic surgical systems are used in minimally invasive medical procedures because of their increased accuracy and expediency relative to handheld surgical instruments. In these robotic surgical systems, a robotic arm supports a surgical instrument having an end effector mounted thereto by a wrist assembly. In operation, the robotic arm is moved to a position over a patient and then guides the surgical instrument into a small incision via a surgical port or a natural orifice of a patient to position the end effector at a work site within the patient's body.

Some robotic surgical systems employ a cart to support the robotic arm and allow a clinician to move the robotic arm to different locations within the operating room. After use of the robotic arm, for cleaning/repair/maintenance, the robotic arm may be detached from the cart and swapped for another robotic arm.

SUMMARY

In an aspect of the present disclosure, a storage assembly for a surgical robotic arm includes a first stand and a second stand each having a front face and a rear face. The rear face of the first stand defines a recess dimensioned for receipt of a first side of a surgical robotic arm, and the front face of the second stand defines a recess dimensioned for receipt of a second side of the surgical robotic arm. The front face of the second stand is configured to couple to the rear face of the first stand. The second stand is configured to support the surgical robotic arm thereon when the second stand is in an upright position.

In aspects, the storage assembly may further include two legs configured to be coupled to a bottom end portion of the second stand.

In another aspect, the two legs may extend laterally outward from the front and rear faces of the second stand to resist tipping of the second stand when the second stand is in the upright position.

In other aspects, the storage assembly may further include a handle coupled to the second stand.

In further aspects, the handle may be coupled to the rear face of the second stand.

In aspects, the handle may be slidably coupled to the second stand.

In another aspect, the handle may be configured to project from a top end portion of the second stand.

In other aspects, the handle may include first and second shafts extending along a height of the second stand, and a crossbar extending transversely between and interconnecting the first and second shafts.

In further aspects, the rear face of the first stand may define a hole, and the front face of the second stand may include a projection configured to complimentarily engage the hole.

In aspects, the front face of the second stand may include a ledge configured to support the surgical robotic arm thereon.

In another aspect, the front face of the first stand may define a cutout in a bottom end portion thereof.

In accordance with another aspect of the disclosure, a method of assembling a surgical robotic arm to a surgical cart is provided and includes moving a first stand from a horizontal position to a vertical position, thereby moving a surgical robotic arm, which is supported by the first stand, to a vertical position; sliding the first stand with the surgical robotic arm into association with a surgical cart to engage the surgical robotic arm with the surgical cart; and removing the first stand from the surgical robotic arm and out of association with the surgical cart.

In aspects, moving the first stand from the horizontal position to the vertical position may include applying an upward-oriented force on a handle attached to the first stand or a second stand.

In another aspect, the method may further include sliding the handle from a retracted position to an extended position prior to applying the upward-oriented force on the handle.

In further aspects, moving the first stand from the horizontal position to the vertical position may include pivoting the first stand about a bottom end portion of the first stand.

In other aspects, the method may further include attaching at least two legs to a bottom end portion of the first stand prior to moving the first stand from the horizontal position to the vertical position.

In aspects, the method may further include detaching a second stand from the first stand to reveal the surgical robotic arm.

In some aspects, detaching the second stand from the first stand may include retracting a projection of the first stand or the second stand from a hole of the other of the first stand or the second stand.

In accordance with yet another aspect of the disclosure, a storage assembly for a surgical robotic arm is provided and includes a stand, at least two legs configured to be coupled to a bottom end portion of the stand, and a handle. The stand includes a front face and a rear face. The front face defines a recess dimensioned for receipt of a surgical robotic arm. The stand is configured to support the surgical robotic arm thereon when the stand is in an upright position. The handle is slidably coupled to the rear face of the stand and configured to selectively project from a top end portion of the stand.

In aspects, the two legs may extend laterally outward from the front and rear faces of the stand to resist tipping of the stand when the stand is in the upright position.

In further aspects of the disclosure, a surgical robotic arm storage assembly is provided and includes a robotic arm and a first stand. The robotic arm includes a base configured to be supported on a surgical cart, and a plurality of elongate members pivotably connected to one another and coupled to the base. The first stand includes a first support column detachably engaged with at least one of the plurality of elongate members, and a first boom extending from a first end portion of the first support column. The first boom is detachably engaged with the base of the robotic arm. The first stand is configured to support the robotic arm on a surface.

In aspects, the first boom may be coupled to the first end portion of the first support column and configured to pivot relative to the first support column into and out of engagement with the base of the robotic arm.

In some aspects, the first stand may include a second boom extending perpendicularly from the first end portion of the first support column. The first boom may be detachably engaged with a first side of the base of the robotic arm, and the second boom may be detachably engaged with a second side of the base of the robotic arm.

In further aspects, the first stand may include a second support column having a first end portion detachably coupled to the first boom.

In other aspects, the surgical robotic arm may include a connector interconnecting the plurality of elongate members and the base. The first end portion of the second support column may be detachably engaged with the connector.

In aspects, the first stand may include a support plate connected to a second end portion of each of the first support column and the second support column.

In some aspects, the second end portion of the second support column may have a pair of spaced-apart legs configured for detachable connection to the support plate.

In further aspects, the surgical robotic arm storage assembly may further include a shipping box having stored therein the surgical robotic arm and the first stand while the first stand is coupled to the surgical robotic arm.

In other aspects, the surgical robotic arm may be pivotably coupled to a lid of the shipping box.

In aspects, the shipping box may include a plurality of side walls detachably coupled to the lid. The side walls may define a cavity having the surgical robotic arm and the first stand disposed therein.

In some aspects, the surgical robotic arm storage assembly may further include a second stand disposed in the shipping box and unconnected to the surgical robotic arm.

In another aspect of the present disclosure, a method of assembling a surgical robotic arm to a surgical cart is provided and includes coupling a first stand to a first surgical robotic arm that is coupled to a surgical cart; removing the coupled surgical robotic arm and first stand from the surgical cart, whereby the first stand supports the surgical robotic arm on a floor; sliding a second stand coupled to a second surgical robotic arm into association with the surgical cart to engage the second surgical robotic arm with the surgical cart; and detaching the second stand from the second surgical robotic arm.

In aspects, the method may further include pivoting the second stand with the second surgical robotic arm from a stored position within a shipping box to an upright position.

In some aspects, the method may further include lifting a plurality of sidewalls of a shipping box from a lid of the shipping box prior to pivoting the second stand with the second surgical robotic arm.

In further aspects, the second stand with the second surgical robotic arm may be pivoted from the stored position to the upright position relative to a lid of the shipping box.

In other aspects, coupling the first stand to the first surgical robotic arm may include coupling a first boom of the first stand to the first surgical robotic arm, whereby a first support column of the first stand extends perpendicularly from the first boom to support the surgical robotic arm on the floor.

In aspects, coupling the first stand to the first surgical robotic arm may further include positioning the first support column under a plurality of elongate members of the surgical robotic arm, and pivoting the first boom relative to the first support column into engagement with the surgical robotic arm.

In some aspects, coupling the first stand to the first surgical robotic arm may further include coupling a second support column of the first stand to the first boom, thereby supporting the first surgical robotic arm on the floor by both the first and second support columns.

In further aspects, engaging the second surgical robotic arm with the surgical cart may include sliding a base of the surgical robotic arm through a receiving slot defined in the surgical cart.

In other aspects, the method may further include pivoting the coupled first surgical robotic arm and first stand relative to a lid of a shipping box from an upright position to a stored position, and lowering a plurality of sidewalls of the shipping box over the coupled first surgical robotic arm and first stand.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or − 10 degrees from true parallel and true perpendicular.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 6A and 6B are front views illustrating the sequential removal of a second stand and a new surgical robotic arm from a shipping box;

FIGS. 8A-8C are side perspective views illustrating the sequential detachment of the second stand of FIGS. 6A and 6B from the surgical robotic arm of FIGS. 6A and 6B;

DETAILED DESCRIPTION

Figure 1:
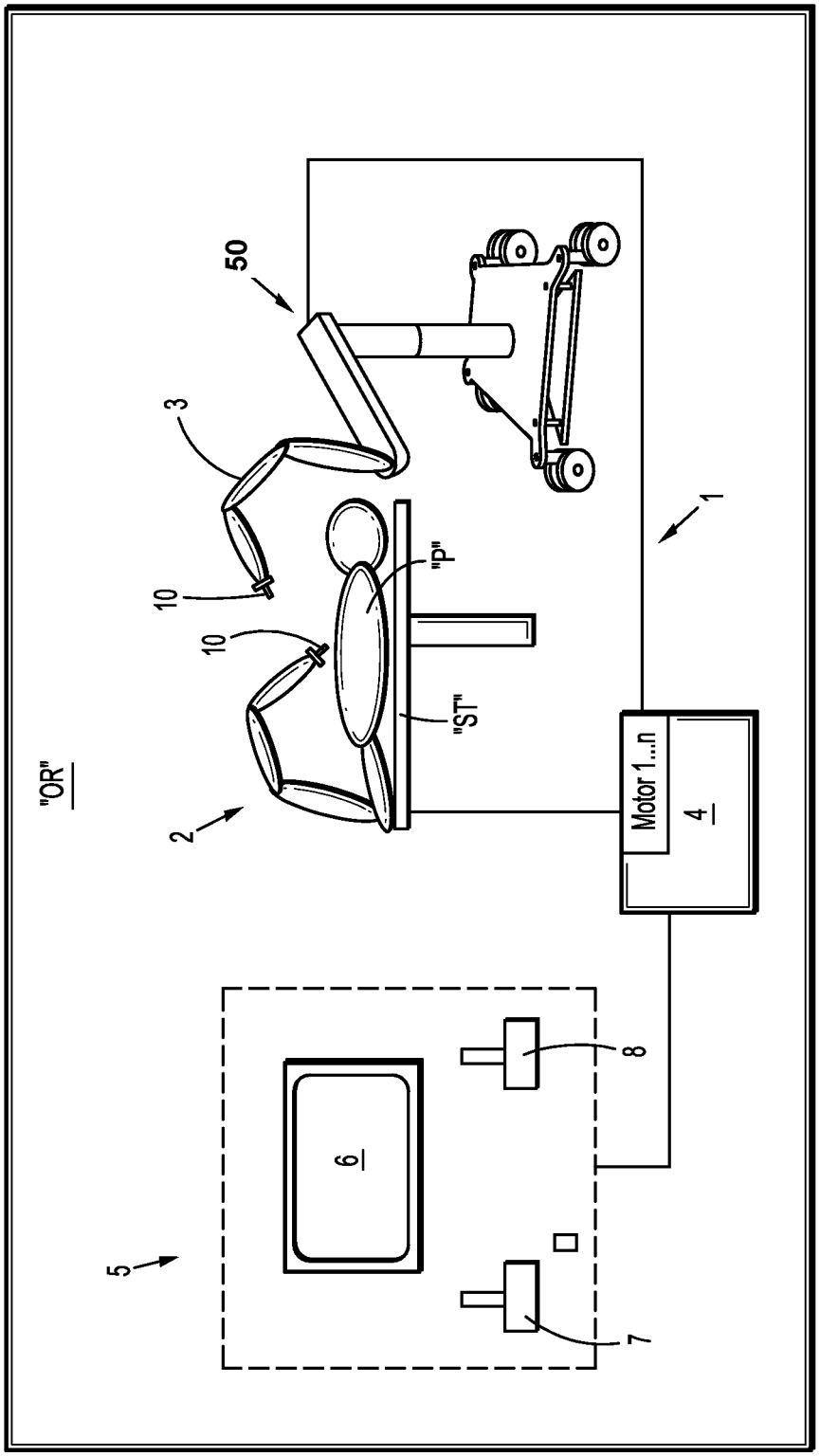
FIG. 1 is a schematic illustration of a robotic surgical system including a surgical robotic arm assembly and a surgical cart in accordance with the present disclosure.

Embodiments of the presently disclosed robotic surgical systems and methods of assembly thereof are described in detail with reference to the drawings, in which like reference numerals designate identical or corresponding elements in each of the several views. As used herein the term "distal" refers to that portion of the robotic surgical system or component thereof, that is closer to the patient, while the term "proximal" refers to that portion of the robotic surgical system or component thereof, that is farther from the patient.

As will be described in detail below, provided are embodiments of a surgical robotic arm storage and replacement assembly including a new surgical robotic arm, first and second stands, and a shipping box. The second stand is in the shipping box and unconnected to the new surgical robotic arm, whereas the first stand comes coupled with the new surgical robotic arm in the shipping box. To replace a used surgical robotic arm supported on a surgical cart, the second stand is coupled to the used surgical robotic arm and the used surgical robotic arm along with the second stand is detached from the surgical cart. The new surgical robotic arm is removed from the shipping box, and utilizing the first stand, the new surgical robotic arm is slid into engagement with the surgical cart. The first stand supports the weight of the new surgical robotic arm to assist a clinician during coupling the new surgical robotic arm to the surgical cart. Upon coupling the new surgical robotic arm to the surgical cart, the first stand may be detached from the surgical robotic arm and stored in the shipping box along with the second stand and the used surgical robotic arm.

Referring initially to FIG. 1, a surgical system, such as, for example, a robotic surgical system 1 is shown. In embodiments, the robotic surgical system 1 is located in an operating room "OR." The robotic surgical system 1 generally includes a plurality of surgical robotic arms 2, 3 having a surgical instrument, such as, for example, an electromechanical instrument 10 removably attached thereto; a surgical cart 50 for supporting the robotic arm(s) 2; a control device 4; and an operating console 5 coupled with the control device 4.

The operating console 5 includes a display device 6, which is set up in particular to display three-dimensional images; and manual input devices 7, 8, by means of which a person (not shown), e.g., a clinician, is able to telemanipulate the robotic arms 2, 3 in a first operating mode, as known in principle to a person skilled in the art. Each of the robotic arms 2, 3 may be composed of a plurality of members, which are connected through joints, as will be described.

The robotic arms 2, 3 may be driven by electric drives (not shown) that are connected to the control device 4. The control device 4 (e.g., a computer) is set up to activate the drives, in particular by means of a computer program, in such a way that the robotic arms 2, 3 and thus the electromechanical instrument 10 (including the electromechanical end effector (not shown)) execute a desired movement according to a movement defined by means of the manual input devices 7, 8. The control device 4 may also be set up in such a way that it regulates the movement of the robotic arms 2, 3 and/or of the drives.

The robotic surgical system 1 is configured for use on a patient "P" lying on a surgical table "ST" to be treated in a minimally invasive manner by means of a surgical instrument, e.g., the electromechanical instrument 10. The robotic surgical system 1 may also include more or less than two robotic arms 2, 3, the additional robotic arms likewise being connected to the control device 4 and being telemanipulatable by means of the operating console 5. A surgical instrument, for example, electromechanical instrument 10 (including the electromechanical end effector), may also be attached to the additional robotic arm.

For a detailed discussion of the construction and operation of a robotic surgical system, reference may be made to U.S. Pat. No. 8,828,023, entitled "Medical Workstation," the entire contents of which are incorporated herein by reference.

Figure 2:
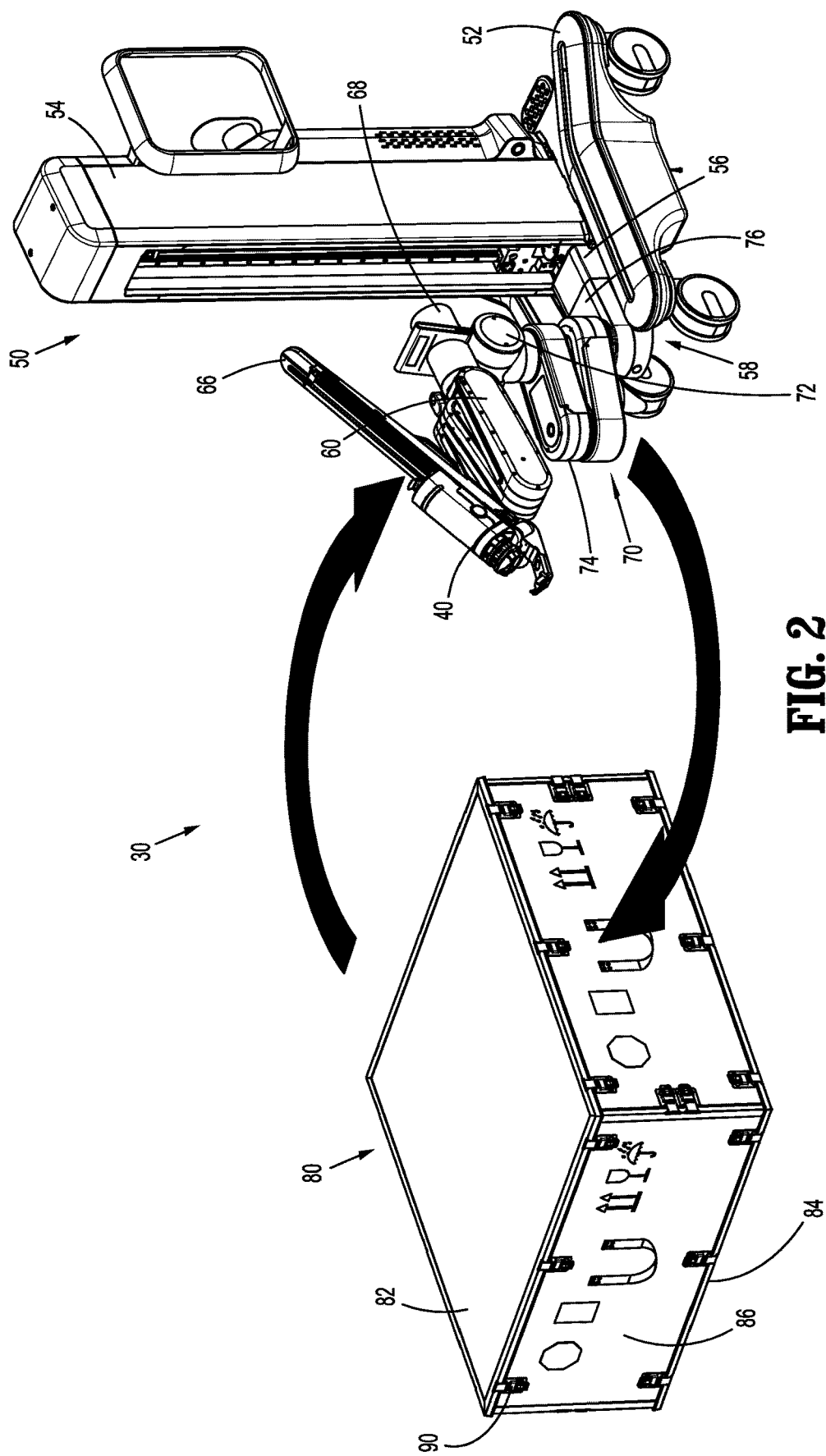
FIG. 2 is a perspective view of the surgical cart and the surgical robotic arm of the robotic surgical system of FIG. 1 including a shipping box of a storage assembly of the present disclosure.

With reference to FIGS. 1 and 2, the surgical cart 50 of the robotic surgical system 1 supports the robotic arms, such as for example, the robotic arm 2. The surgical cart 50 may incorporate the control device 4. In some aspects, the robotic arms 2 may be coupled to the surgical table "ST." The surgical cart 50 is configured to move the robotic arm 2 to a selected position within the operating room "OR" and to provide the capability of adjusting the height of the robotic arm 2. The surgical cart 50 generally includes a cart base 52, a support column 54 extending vertically (e.g., perpendicularly) from the cart base 52, and a carriage or slider 56 slidably supported on the column 54 and configured for supporting the robotic arm 2 thereon. The cart base 52 defines a slot 58 through which the slider 56 extends.

Figure 3:
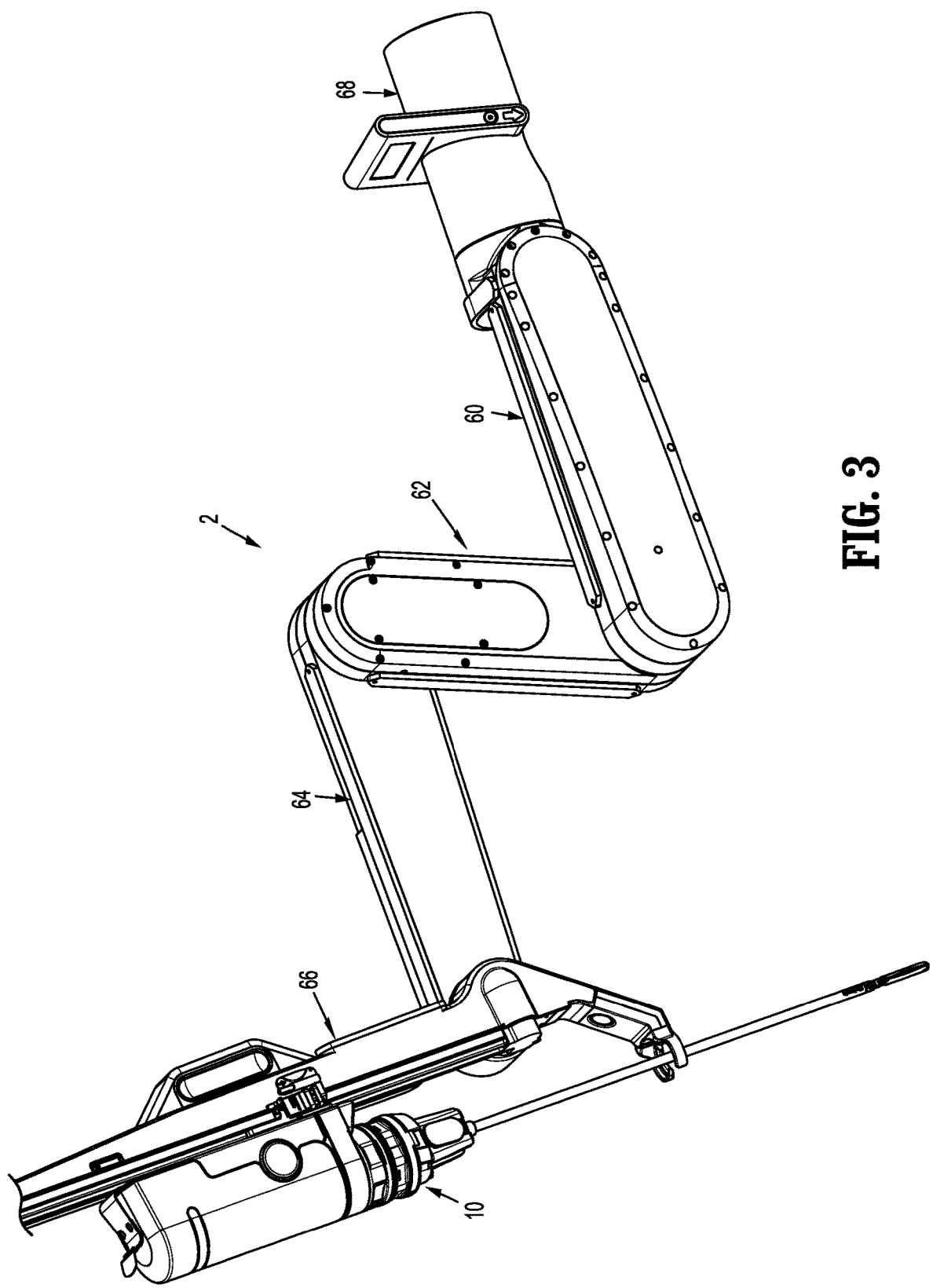
FIG. 3 is a side perspective view of the surgical robotic arm storage assembly of FIG. 2 coupled to and supporting a surgical instrument.

With reference to FIGS. 2 and 3, the surgical robotic arm 2 is configured to support an instrument drive unit 40 thereon and to selectively move the instrument drive unit 40 and the attached surgical instrument 10 in a plurality of orientations relative to a small incision in a patient. The robotic arm 2 includes a plurality of elongate members or links 60, 62, 64, 66 pivotably connected to one another to provide varying degrees of freedom to the robotic arm 2. In particular, the robotic arm 2 includes a first elongate member 60, a second elongate member 62, a third elongate member 64, and a fourth elongate member or rail 66. The first elongate member 60 is rotatably coupled to a shaft member 68.

The shaft member 68 of the surgical robotic arm 2 is supported on a base 70 of the robotic arm 2. The base 70 of the robotic arm 2 may include an axle 72 on which the shaft member 68 is supported, a plurality of links 74 coupled to the axle 72, and a connector 76 coupled to the plurality of links 74 of the base 70. The plurality of links 74 are configured to pivot relative to one another to adjust a position of the surgical instrument 10. The connector 76 of the base 70 is configured to be mechanically and electrically detachably coupled to the cart base 52.

With reference to FIGS. 2 and 4A-4C, the surgical robotic system 1 includes a surgical robotic arm assembly 30 that includes the surgical robotic arm 2; and a storage assembly that includes first and second stands 100, 200 (FIGS. 6A and 6B), and optionally a shipping box 80. The surgical robotic arm 2 and the first and second stands 100, 200 may be stored in the shipping box 80 prior to use. The first stand 100 may be stored in the shipping box 80 unconnected from a new surgical robotic arm 3, whereas the second stand 200 (FIGS. 6A and 6B) may be detachably fixed to the new surgical robotic arm 3. Due to the first and second stands 100, 200 being similar or the same as one another, only the first stand 100 will be described in detail herein.

Figure 4C:
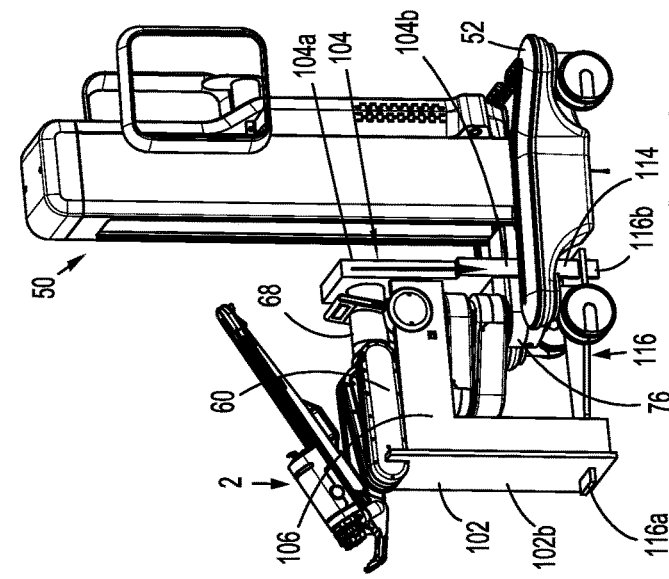
FIGS. 4A-4C are side perspective views illustrating a sequential assembly of a first stand to the surgical robotic arm of FIG. 2.
Figure 4B:
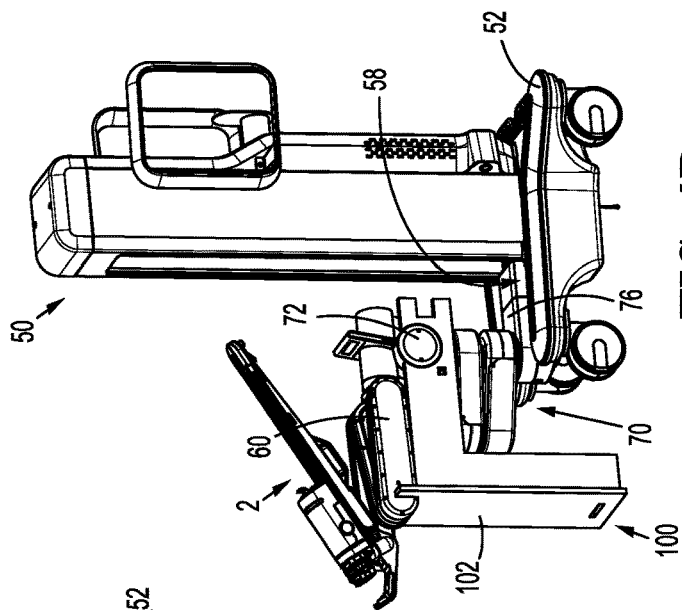
Figure 4A:
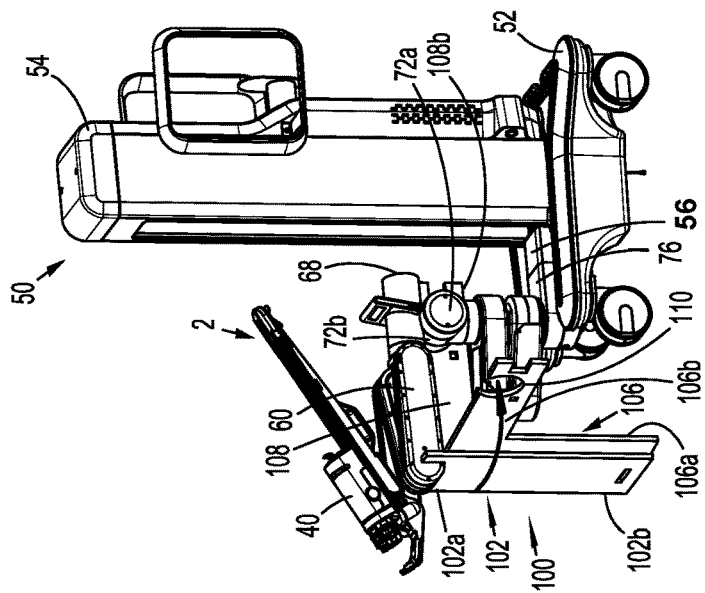

The first stand 100 includes first and second vertically-extending support columns 102, 104, and first and second booms 106, 108 extending between and interconnecting first and second support columns 102, 104. The first and second supports columns 102, 104 each has a first end portion 102a, 104a configured to support the plurality of elongate members 60, 62, 64 (FIG. 2) of the surgical robotic arm 2 thereon when the elongate members 60, 62, 64 are disposed in a collapsed state, as shown in FIGS. 4A-4C. The first and second supports columns 102, 104 each has a second end portion 102b, 104b to be positioned on a surface (e.g., a floor of an operating room). The first and second support columns 102, 104 are configured to support the surgical robotic arm 2 so that the connector 76 of the surgical robotic arm 2 is maintained at the same height as the cart base 52 when the first stand 100 is coupled to the surgical robotic arm 2.

Each of the first and second booms 106, 108 has a first segment 106a, 108a coupled to the first end portion 102a of the first support column 102, and a second segment 106b extending perpendicularly relative to the first and second support columns 102, 104. The first segment 106a of the first boom 106 is hingedly coupled to the first support column 102, such that the first boom 106 may be pivoted between a first position (FIG. 4A) out of engagement with the base 70 of the surgical robotic arm 2, and a second position (FIG. 4B) into engagement with the base 70 of the surgical robotic arm 2. The second segment 106b, 108b of each of the first and second booms 106, 108 defines a cutout 110 configured to receive an opposite side 72a, 72b of the axle 72 of the base 70 of the surgical robotic arm 2.

With reference to FIG. 4C, the second support column 104 of the first stand 100 has a first end portion 104a detachably coupled to the first and second booms 106, 108 via any suitable fastening engagement. For example, the second end portion 106b, 108b of each of the first and second booms 106, 108 may be frictionally received in corresponding slots (not explicitly shown) defined in the first end portion 104a of the second support column 104 (e.g., in a tongue and groove arrangement). The first end portion 104a of the second support column 104 may also be detachably engaged with the connector 76 of the surgical robotic arm 2 to further secure the connection between the first stand 100 and the surgical robotic arm 2.

The second support column 104 may have a second end portion 104b having a pair of spaced-apart legs 114 configured to extend into the slot 58 (FIG. 2) of the cart base 52 and straddle the carriage 56 of the surgical cart 50. The first stand 100 may further include a support plate 116 having a first end portion 116a and a second end portion 116b. The first end portion 116a is configured for receipt in an opening defined in the second end portion 102b of the first support column 102. The second end portion 116b of the support plate 116 defines a pair of spaced-apart openings configured for removable receipt of the spaced-apart legs 114 of the second support column 104. It is contemplated that the support plate 116 may be flexible along its length to facilitate assembly of the first and second support columns 102, 104 thereto.

With reference to FIGS. 2, 6A, and 6B, the shipping box 80 of the surgical robotic arm assembly 30 has a top lid 82, a bottom lid 84, and a plurality of side walls 86 collectively defining a cavity 88. The top and bottom lids 82, 84 are both detachable from the side walls 86. For example, the shipping box 80 may include a plurality of toggle latches 90 connecting the top and bottom lids 82, 84 to the side walls 86. Other types of fastening engagements are also contemplated. The surgical robotic arm 2 is pivotably coupled to an inner surface of the bottom lid 84 of the shipping box 80, such that the surgical robotic arm 2 is configured to pivot between a flat, stored position (FIG. 6A) and a deployed, upright position (FIG. 6B) via a pivot member 92 (FIG. 6B).

An exemplary method of assembling a new surgical robotic arm 3 to a surgical cart 50 utilizing the first and second stands 100, 200 described above will now be described. It can be assumed that the method described herein may be employed by a single clinician. With reference to FIGS. 4A-4C, the carriage 56 of the cart base 52 is lowered along the column 54 of the surgical cart 50 to a position within the slot 58 of the cart base 52. With the plurality of elongate members 60, 62, 64 of the surgical robotic arm 2 in a collapsed state (e.g., in a side-by-side configuration), the second boom 108 of the first stand 100 is moved underneath the plurality of elongate members 60, 62, 64 and the second side 72b of the axle 72 of the surgical robotic arm 2 is received in the cutout (not explicitly shown) in the second boom 108. The first boom 106 is pivoted into engagement with the surgical robotic arm 2, whereby the first side 72a of the axle 72 of the surgical robotic arm 2 is received in the cutout 110 in the first boom 106. The first end portion 116a of the support plate 116 is received in the opening in the second end portion 102b of the first support column 102. The first end portion 104a of the second support column 104 is connected with the second end portions 106b, 108b of the first and second booms 106, 108 while the spaced-apart legs 114 of the second end portion 104b of the second support column 104 are inserted into the corresponding openings in the second end portion 116b of the support plate 116.

Figure 5A:
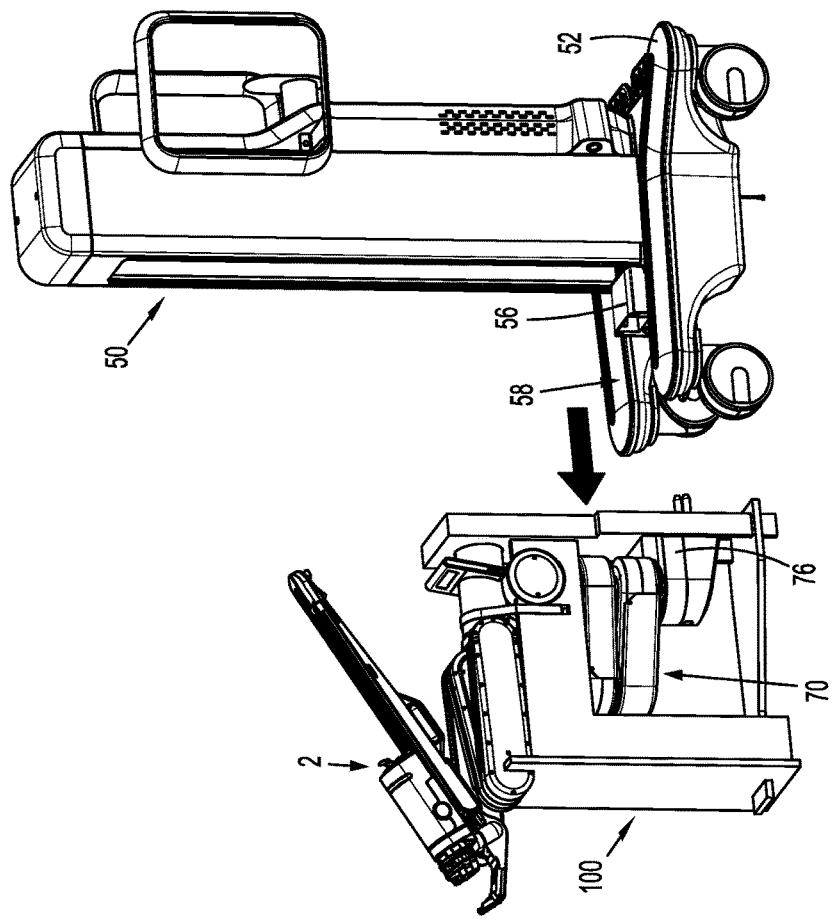
FIGS. 5A and 5B are side perspective views illustrating the sequential removal of the first stand with the surgical robotic arm from the surgical cart of FIG. 2.
Figure 5B:
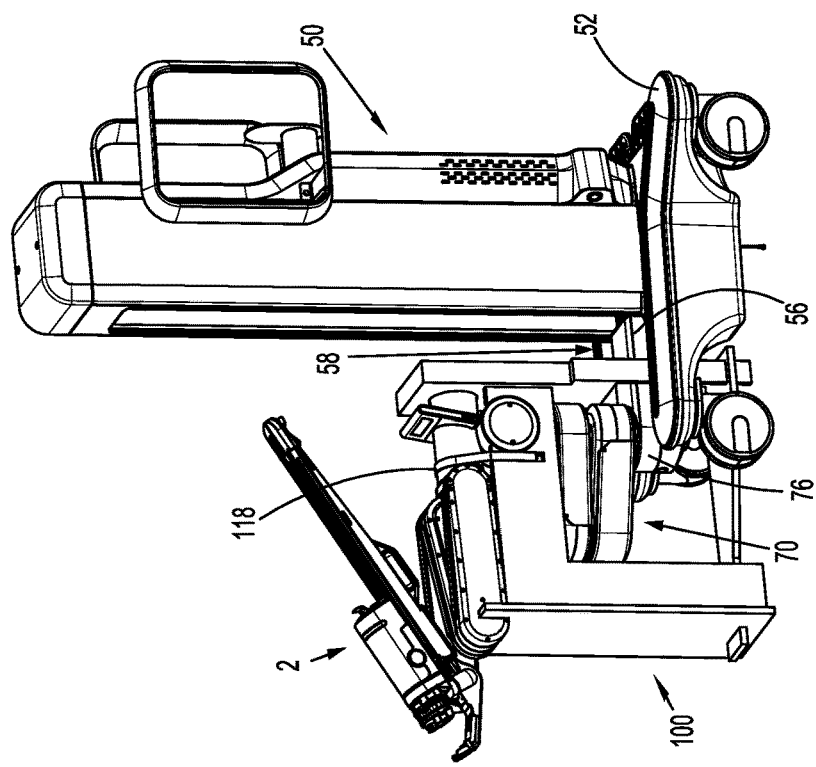

With reference to FIGS. 5A and 5B, a strap 118 may be used to better secure the surgical robotic arm 2 to the first stand 100. With the surgical robotic arm 2 secured and supported by the first stand 100, the connector 76 of the base 70 of the surgical robotic arm 2 is disconnected from the carriage 56 of the surgical cart 50. The first stand 100, carrying the surgical robotic arm 2, is slid away from the surgical cart 50 and out of the slot 58 in the cart base 52.

With reference to FIGS. 6A and 6B, after detaching the used surgical robotic arm 2 from the surgical cart 50, a new surgical robotic arm 3 may be attached to the surgical cart 50. In particular, after having removed the top lid 82 (FIG. 2) of the shipping box 80, the side walls 86 of the shipping box 80 are removed from the bottom lid 84 to uncover the new surgical robotic arm 3. Due to the second stand 200 (preassembled) and the new surgical robotic arm 3 being shipped in a coupled state, erecting the new surgical robotic arm 3 from the stored position is made easy by simply pivoting the second stand 200 relative to the bottom lid 84 to move the new surgical robotic arm 3 from the stored position to the upright position, as shown in FIG. 6B.

Figure 7A:
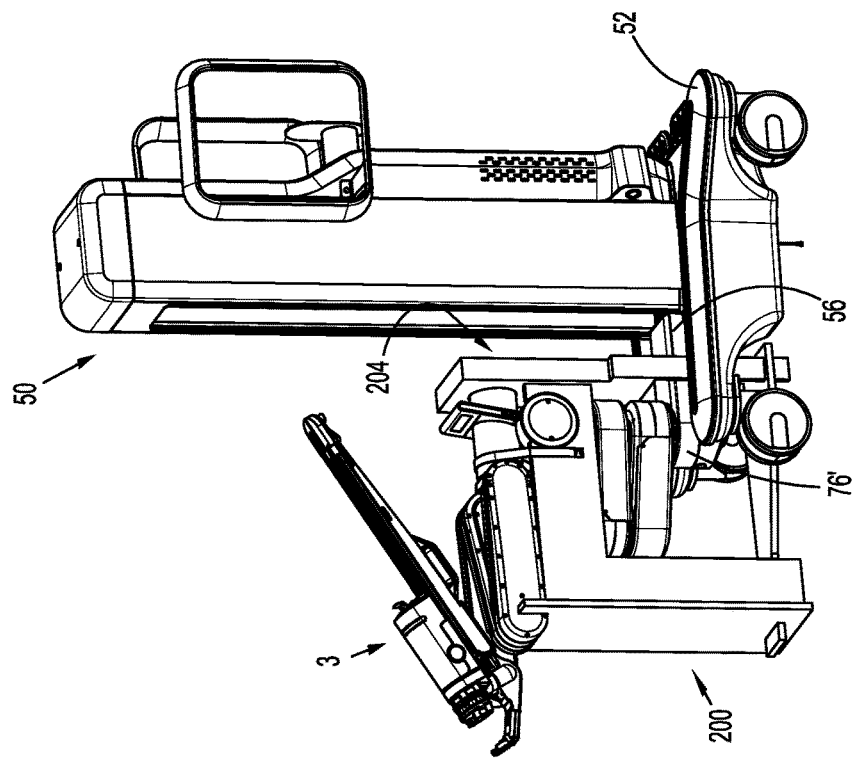
FIGS. 7A and 7B are side perspective views illustrating the sequential coupling of the surgical robotic arm of FIGS. 6A and 6B to the surgical cart of FIG. 2.
Figure 7B:
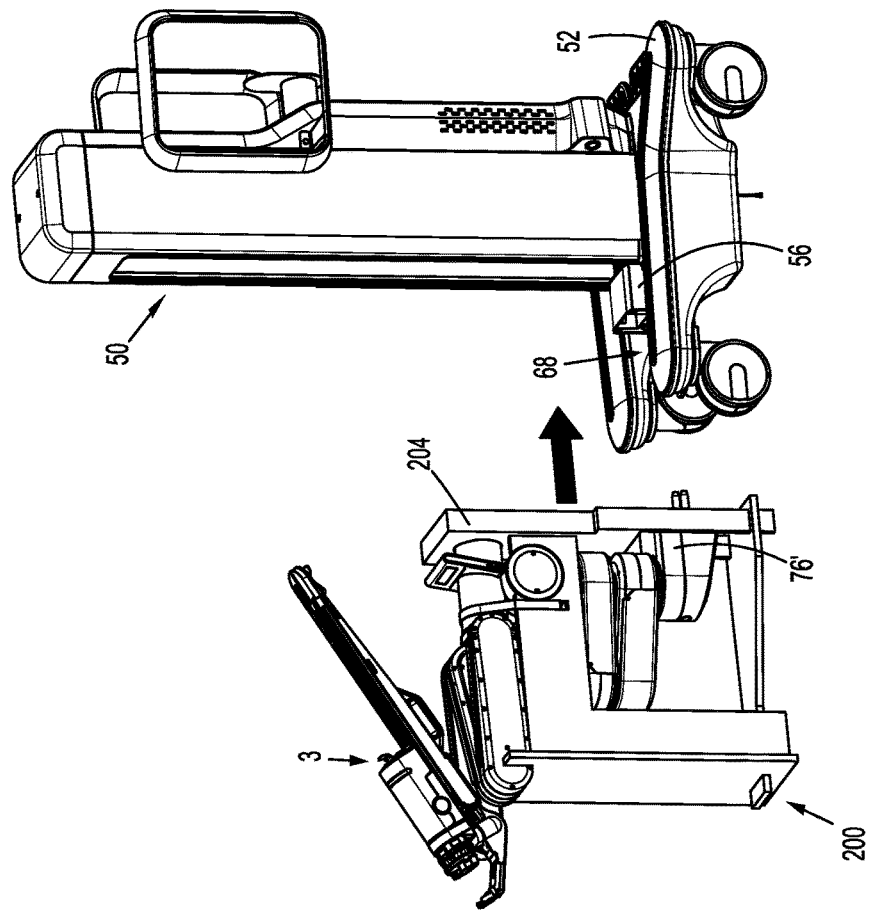

With reference to FIGS. 7A and 7B, with the new surgical robotic arm 3 in the upright position and being supported on the second stand 200, the second stand 200 is moved along a floor (e.g., an operating room floor) to carry the new surgical robotic arm 3 toward the surgical cart 50. The second support column 204 of the second stand 200 is moved into the slot 58 in the cart base 52 to engage the connector 76' of the new surgical robotic arm 3 with the carriage 56 of the surgical cart 50, thereby transferring the weight of the new surgical robotic arm 3 from the second stand 200 to the carriage 56 of the surgical cart 50.

With reference to FIGS. 8A-8C, with the new surgical robotic arm 3 engaged with and supported by the surgical cart 50, the second stand 200 may be detached from the new surgical robotic arm 3. In particular, the second support column 204 of the second stand 200 is disengaged from the first and second booms 206, 208 of the second stand 200 and the support plate 216 of the second stand 200. The first boom 206 is pivoted out of engagement with the axle 72' of the new surgical robotic arm 3, and the second boom 208 and the first support column 202 are moved out of engagement with the surgical robotic arm 3.

Figure 9B:
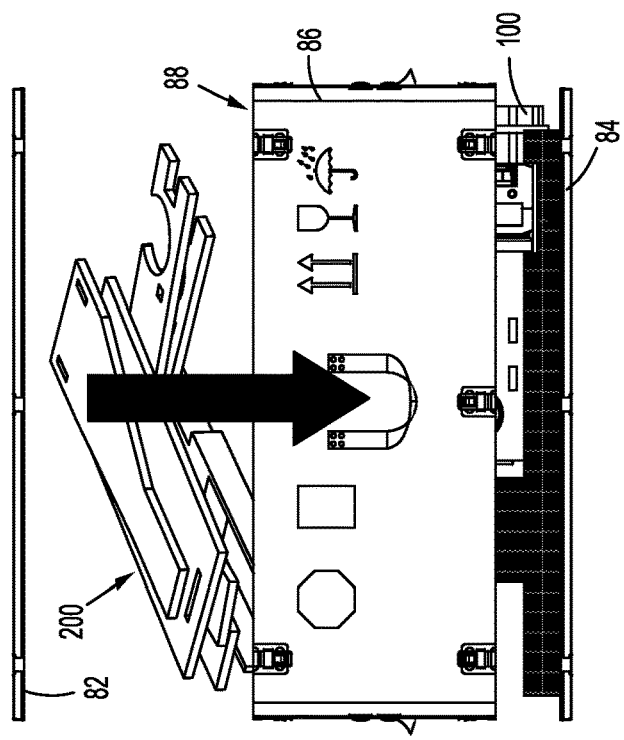
FIGS. 9A and 9B are front views illustrating the sequential storing of the first and second stands in the shipping box of FIGS. 6A and 6B.
Figure 9A:
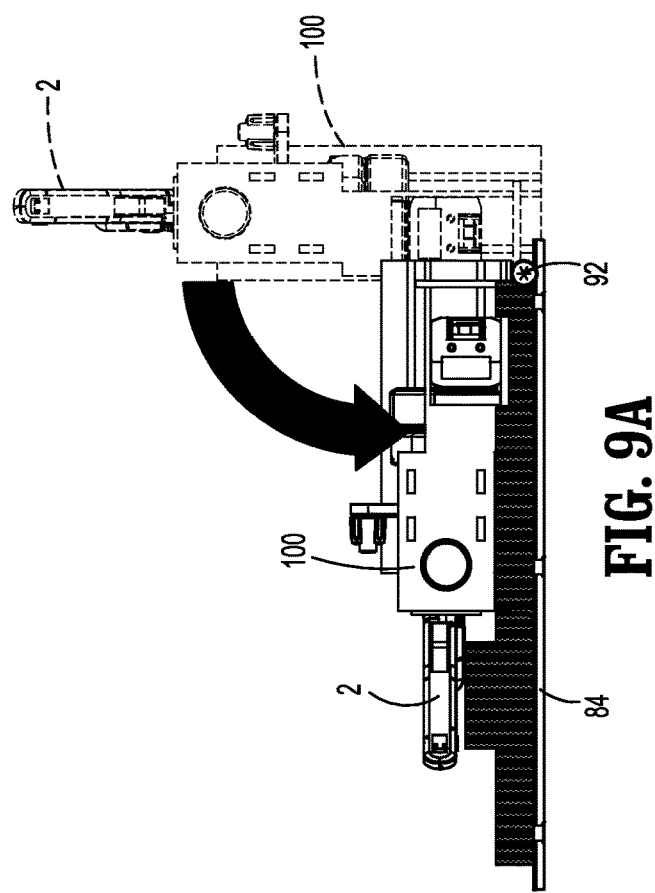

With reference to FIGS. 9A and 9B, to store the used surgical robotic arm 2, the first stand 100 is coupled to the hinge or pin 92 of the bottom lid 84 of the shipping box 80 and pivoted relative to the bottom lid 84 to move the old or used surgical robotic arm 2 from the upright position to the stored position. The side walls 86 are lowered over the first stand 100 and the used surgical robotic arm 2 and into engagement with the bottom lid 84. With the side walls 86 engaged with the bottom lid 84, the second stand 200 is lowered into the cavity 88 defined by the side walls 86, and the top lid 82 is closed.

Figure 10:
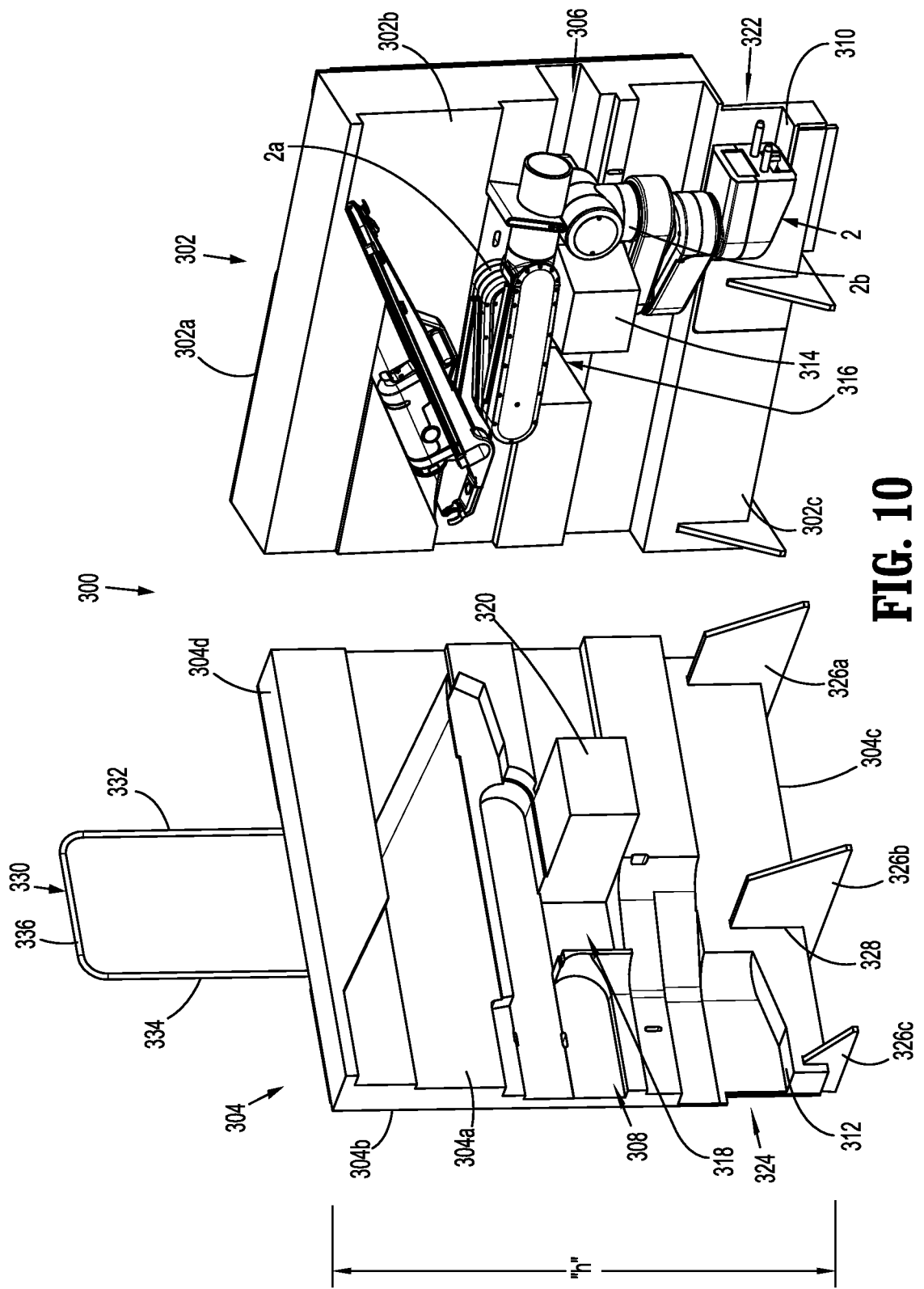
FIG. 10 is a front, perspective view, with parts separated, illustrating another embodiment of a storage or shipping assembly for a surgical robotic arm.

FIG. 10 illustrates an embodiment of a storage or shipping assembly 300 for a surgical robotic arm, such as, for example, the surgical robotic arm 2. The storage assembly 300 generally includes first and second stands 302, 304 that when coupled to one another cover and encase the surgical robotic arm 2 therebetween for shipping, storage, and the like. The first and second stands 302, 304 are each illustrated as having a square shape, but it is contemplated that the first and second stands 302, 304 may assume any suitable shape, such as, for example, round, triangular, or the like. The first and second stands 302, 304 each have a front face 302a, 304a and a rear face 302b, 304b, opposite the front face 302a, 304a. The front face 302a of the first stand 302a and the rear face 304b of the second stand 304 may be fabricated from a hard material, such as a wood, metal, or plastic, and the rear face 302b of the first stand 302 and the front face 304a of the second stand 304 may be fabricated from a relatively softer, more accommodating material, such as, for example, polystyrene foam.

The rear face 302b of the first stand 302 and the front face 304a of the second stand 304 define a recess 306, 308 therein. The recess 306 of the first stand 302 is dimensioned for receipt of a first side 2a of the surgical robotic arm 2 and the recess 308 of the second stand 304 is dimensioned for receipt of a second side 2b of the surgical robotic arm 2. The recesses 306, 308 are shaped to match or compliment the overall shape of the surgical robotic arm 2 when in a collapsed state, as shown in FIG. 10. The first and second stands 302, 304 each define a plurality of ledges 310, 312 on which the surgical robotic arm 2 may be supported when the stands 302, 304 are in a vertical or upright position. The rear face 302b of the first stand 302 defines a hole 314 and includes a projection 316, and the front face 304a of the second stand 304 also defines a hole 318 and includes a projection 320. The hole 316 of the first stand 302 is configured to complimentarily receive the projection 320 of the second stand 304, and the hole 318 of the second stand 304 is configured to complimentarily receive the projection 314 of the first stand 302 to allow for the first and second stands 302, 304 to selectively couple to one another. The front face 302a of the first stand 302 defines a cutout 322 in a bottom end portion 302c thereof, and the rear face 304b of the second stand 304 defines a cutout 324 in a bottom end 304c portion thereof. The cutouts 322, 324 allow for the first or second stands 302, 304 to be received in the slot 58 (FIG. 5B) in the cart base 52 during assembly of the surgical robotic arm 2 with the surgical cart 50. In aspects, one or both of the stands 302, 304 may have a plurality of straps (not shown) to assist in securing the surgical robotic arm 2 thereto.

The storage assembly 300 may further include a plurality of legs 326a, 326b, 326c for supporting the first stand 302 and/or the second stand 304 in the upright position and for preventing tipping thereof. For example, the second stand 304 may include first and second larger legs 326a, 326b and a third smaller leg 326c each configured to be received in corresponding slits 328 defined in the bottom end portion 304c of the second stand 304. The legs 326a, 326b, 326c extend laterally outward from the front and rear faces 304a, 304b of the second stand 304 to resist tipping of the second stand 304 when the second stand 304 is in the upright position. The stands 302, 304 may assume any suitable shape, such as, for example, trapezoidal, triangular, semi-circular, or the like. In other aspects, the stands 302, 304 may be equipped with wheels.

The second stand 304 includes a telescoping handle 330 slidably coupled to the rear face 304b thereof. The handle 330 is configured to move relative to the second stand 304 between a retracted position, in which the handle 304 does not project from a top end portion 304d of the second stand 304, and an extend position, in which the handle 330 projects from the top end portion 304d of the second stand 304. The handle 330 includes first and second shafts 332, 334 extending parallel with a height "h" of the second stand 304, which is defined between the top and bottom end portions 304c, 304d thereof. The first and second shafts 332, 334 are spaced laterally from one another and are slidably coupled to the rear face 304b of the second stand 304 via an eyebolt, a clip, or the like. The handle 330 further includes a crossbar 336 extending transversely between and inter-connecting ends of the first and second shafts 332, 334. The cross bar 336 may be monolithically formed with the first and second shafts 332, 334. In some aspects, the first and second shafts 332, 334 may be angled relative to one another (e.g., splayed outwardly) or may be non-linear along their lengths, such as, for example, curved or bent.

In use, the surgical robotic arm 2 may be assembled to the surgical cart 50 (FIG. 2) with the assistance of the storage assembly 300. In particular, with the storage assembly 300 in a horizontal or stored position, the first stand 302 may be detached from the second stand 304 by removing the projections 314, 320 from the corresponding holes 316, 318 to reveal the surgical robotic arm 2. The legs 326a, 326b, 326c may be attached to the bottom end portion 304c of the second stand 304 while the second stand 304 is in the horizontal position.

With the first stand 302 removed from the second stand 304, the second stand 304 may be moved to a vertical or upright position. In aspects, the storage assembly 300 may be moved to the upright position while the first and second stands 302, 304 remain coupled to one another. Due to the surgical robotic arm 2 being supported by the second stand 304, moving the second stand 304 to the upright position also moves the surgical robotic arm 2 to the upright position. To move the second stand 304 to the upright position, the handle 330 is moved from the retracted position to the extended position and an upward-oriented force is applied to the crossbar 336 of the handle 330. The application of the upward-oriented force on the handle 330 pivots the second stand 304 from the horizontal position to the vertical position about the bottom end portion 304c of the second stand 304.

The second stand 304, with the surgical robotic arm 2 supported thereon, may be slid along a surface toward the surgical cart 50 (FIG. 2). The second stand 304 is slid into association with the surgical cart 50 to engage the surgical robotic arm 2 with the surgical cart 50. Upon engaging the surgical robotic arm 2 with the surgical cart 50, the second stand 304 may be detached from the surgical robotic arm 2 and moved out of association with the surgical cart 50 by sliding the second stand 304 proximally relative to the surgical robotic arm 2.

While the storage assemblies of the present disclosure have been shown and described for use in cooperation with surgical robotic arm 2 that are supported on surgical carts 50 and the like, it is contemplated, and within the scope of the present disclosure for the storage assemblies to be used in cooperation with surgical robotic arms 2 that are directly/indirectly connected to or supported on an operating room bed or table.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

The invention claimed is:

1. A surgical robotic arm storage assembly, comprising:
   a robotic arm including:
      a base configured to be supported on a surgical cart; and
      a plurality of elongate members pivotably connected to one another and coupled to the base; and
   a first stand including:
      a first support column detachably engaged with at least one of the plurality of elongate members;
      a first boom extending from a first end portion of the first support column and detachably engaged with the base of the robotic arm, wherein the first stand is configured to support the robotic arm on a surface; and
      a second boom extending perpendicularly from the first end portion of the first support column, the first boom detachably engaged with a first side of the base of the robotic arm, and the second boom detachably engaged with a second side of the base of the robotic arm.

2. The surgical robotic arm storage assembly according to claim 1, wherein the first boom is coupled to the first end portion of the first support column and configured to pivot relative to the first support column into and out of engagement with the base of the robotic arm.

3. A surgical robotic arm storage assembly, comprising:
   a robotic arm including:
      a base configured to be supported on a surgical cart;
      a plurality of elongate members pivotably connected to one another and coupled to the base; and
   a first stand including:
      a first support column detachably engaged with at least one of the plurality of elongate members;
      a second support column having a first end portion detachably coupled to the first boom; and
      a first boom extending from a first end portion of the first support column and detachably engaged with the base of the robotic arm, wherein the first stand is configured to support the robotic arm on a surface; and
   a connector interconnecting the plurality of elongate members and the base, the first end portion of the second support column detachably engaged with the connector.

4. A surgical robotic arm storage assembly, comprising:
   a robotic arm including:
      a base configured to be supported on a surgical cart; and
      a plurality of elongate members pivotably connected to one another and coupled to the base; and
   a first stand including:
      a first support column detachably engaged with at least one of the plurality of elongate members;
      a second support column having a first end portion detachably coupled to the first boom, and a second end portion;
      a support plate connected to a second end portion of each of the first support column and the second support column; and
      a first boom extending from a first end portion of the first support column and detachably engaged with the base of the robotic arm, wherein the first stand is configured to support the robotic arm on a surface;
      wherein the second end portion of the second support column has a pair of spaced-apart legs configured for detachable connection to the support plate.

5. The surgical robotic arm storage assembly according to claim 1, further comprising a shipping box having stored therein the surgical robotic arm and the first stand while the first stand is coupled to the surgical robotic arm.

6. The surgical robotic arm storage assembly according to claim 5, wherein the surgical robotic arm is pivotably coupled to a lid of the shipping box.

7. The surgical robotic arm storage assembly according to claim 6, wherein the shipping box includes a plurality of side walls detachably coupled to the lid, the plurality of side walls defining a cavity having the surgical robotic arm and the first stand disposed therein.

8. The surgical robotic arm storage assembly according to claim 5, further comprising a second stand disposed in the shipping box and unconnected to the surgical robotic arm.

* * * * *